United States Patent [19]

Banker et al.

[11] Patent Number: 5,580,974
[45] Date of Patent: Dec. 3, 1996

[54] MICROFIBRILLATED OXYCELLULOSE DISPERSIONS

[75] Inventors: Gilbert S. Banker, Iowa City; Vijay Kumar, Coralville, both of Iowa

[73] Assignee: Biocontrol Incorporated, Iowa City, Iowa

[21] Appl. No.: 420,089

[22] Filed: Apr. 11, 1995

Related U.S. Application Data

[62] Division of Ser. No. 100,979, Aug. 3, 1993, Pat. No. 5,405,953.

[51] Int. Cl.$^6$ .......................... C08B 11/00; C07H 15/04; A61K 6/00
[52] U.S. Cl. .............................. 536/56; 536/84; 536/120; 536/124; 400/401
[58] Field of Search .......................... 536/56, 84, 120, 536/124; 400/401

[56] References Cited

U.S. PATENT DOCUMENTS

| | | | |
|---|---|---|---|
| 3,364,200 | 1/1968 | Ashton et al. | 536/56 |
| 4,022,965 | 5/1977 | Goheen et al. | 536/56 |
| 5,134,229 | 7/1992 | Saferstein et al. | 536/56 |

*Primary Examiner*—Nathan M. Nutter
*Attorney, Agent, or Firm*—Robert D. Katz

[57] ABSTRACT

Microfibrillated oxycellulose suitable for use as a carrier in agricultural, cosmetic, and topical and transdermal drug products, and as a binder and disintegrant in the making of tablets, is prepared by the oxidation of cellulosic materials with persulfate salts in water, with or without the presence of an aqueous inorganic acid, or in glacial or aqueous acetic acid.

17 Claims, 3 Drawing Sheets

MICROFIBRILLATED OXYCELLULOSE DISPERSIONS

This is a division of application Ser. No. 08/100,979 filed Aug. 3, 1993, now U.S. Pat. No. 5,405,953.

FIELD OF THE INVENTION

This invention relates to methods of preparing oxidized cellulose derivatives, and to microfibrillated oxycellulose derivatives.

BACKGROUND OF THE INVENTION

Compared to microcrystalline cellulose and cellulosic derivatives, such as ethers and esters that are widely used in the cosmetic and pharmaceutical industries, oxidized celluloses have received relatively little attention. The various applications of oxidized celluloses (or oxycelluloses, as they are often called) in medical and related areas include their use as: (1) coating materials for ferric and aluminum salt granules in the formulation of microencapsulated astringent hemostatic agents; (2) bodying agents in the preparation of cosmetic and pharmaceutical preparations; (3) biocompatible antihemorrhegic absorbable materials for wounds and to stop bleeding during surgery; (4) fibrin formation-accelerating agents; (5) deodorants for absorbent pads (e.g., dressing, diapers and catamenials); and (6) biocompatible mold release agents or donning powders and medical lubricants for surgical gloves, and the like. However, the continuing lack of the wide-spread use of oxycelluloses as a pharmaceutical aids can be attributed to the unavailability of methods to produce oxycelluloses that are stable during storage at room temperature and at elevated temperatures, and are compatible with a wide variety of chemicals.

Several strategies have been developed for the preparation of oxycelluloses from cellulosic materials using a variety of oxidants. These oxidants include gaseous oxygen, hydrogen peroxide, peracetic acid, chlorine dioxide, nitrogen dioxide and/or dinitrogen tetraoxide, persulfates, permanganate, dichromatesulfuric acid, and alkali or alkaline earth metal hypohalites or periodates. [T. P. Nevell, in *Cellulose Chemistry and its Applications:* 1, *Cellulose,* T. P. Nevell et al., eds., Ellis Horwood Ltd., England (1985) at Ch. 10.] Of these, oxycelluloses prepared utilizing alkali metal periodates, nitrogen dioxide, gaseous oxygen, hydrogen peroxide, and alkali or alkaline earth metal hypohalites have been extensively studied. The periodate-derived oxycelluloses are extremely sensitive to alkali and undergo condensation and other reactions characteristic of aldehyde functional groups.

The oxycellulose products, prepared using nitrogen dioxide and/or dinitrogen tetraoxide in the liquid or gaseous state, are also very sensitive to alkali, and have a high free carboxylic acid content. The latter have been reported to cause gradual deterioration and color change of the product during storage. According to German Patent No. 2,061,796, the room temperature stability of the nitrogen oxide-derived oxycellulose can be improved by treating the product with alkali metal borohydride in an aqueous-alcohol medium, followed by washing the solid with dilute acid, drying, and sterilization.

U.S. Pat. No. 3,364,200 discusses the production of stable nitrogen oxide and/or dinitrogen tetraoxide-derived oxidized cellulose by washing the product first with a non-aqueous solvent (carbon tetrachloride or tetrachlorodifluoroethane), then with an aqueous-alcohol solution, and finally with a non-aqueous solvent having an affinity for water. The oxidation of cellulose by gaseous oxygen and/or hydrogen peroxide, in the presence of alkali, has been reported to produce oxycelluloses that have a high amount of ketone groups and some aldehyde and carboxylic acid groups. Studies have reported that this method is highly non-reproducible, probably due to the strong catalytic effect of the metal ions present in the water used as the reaction medium. It is practically impossible to completely eliminate such ions or to assure their presence, in precisely the same amounts, in consecutive experiments. The hypochlorite-oxycelluloses, prepared under mild acidic conditions, are known to degrade and turn yellow during storage, whereas products prepared using alkaline solutions are quite stable. See T. P. Nevell, in *Cellulose Chemistry and its Applications:* 1. *Cellulose,* T. P. Nevell et al., eds., Ellis Horwood Ltd., England (1985) at Ch. 10.

U.S. Pat. No. 4,480,089 (Chen) discusses the preparation of a cellulose product suitable for use in cosmetics or pharmaceuticals using an excess of hypochlorite solution, having an initial pH of about 12, at various temperatures, and by allowing the pH of the reaction solution to drop to as low as about 2. The tendency of the product to undergo color changes during storage is not mentioned. Other methods used to prepare oxycelluloses include oxidation of cotton linters with a $HNO_3$—$NaNO_2$ mixture, followed by controlled heterogenous hydrolysis, or by stabilization and sterilization, or by oxidation with an acidic $K_2Cr_2O_7$—$NO_2$ mixture.

The first use of persulfate in the oxidation of cellulose was reported by Ditz, *J. Prakt. Chem.,* 78, 343 (1908). Since then, very little work has been reported. According to F. H. Chowdhury et al., *Sci. Res.,* 3, 22 (1966), oxidation of cellulose by persulfate can be achieved in neutral or acidic medium only in the presence of traces of silver ions.

I. Rusznak et al., *Kolorisztikai Ertesito,* 10, 38 (1968) and A. Kantruch et al., *Kolorisztikai Ertesito,* 10, 208 (1968) discuss the reaction of α-cellulose with aqueous sodium persulfate for 1–10 hours at 50°–70° C. at pH 4–10, using a persulfate concentration of 0.025M, 0.05M, 0.1M or 0.15M and α weight-to-volume ratio of 1:100 α-cellulose:sodium persulfate solution. However, neither method appears to produce oxycellulose products suitable for use in pharmaceutical preparations, but yield instead unruptured or long fibers, with a low surface area. These fibers do not disperse in water and do not coalesce.

Therefore, there appears to be an unfilled need for a method to oxidize cellulosic materials to oxycellulosic products which can serve as carriers for a wide variety of bioactive materials in substantive, controlled and/or sustained release formulations.

SUMMARY OF THE INVENTION

The present invention provides a method for making oxycellulose comprising oxidizing a cellulosic material with persulfate salt in (a) water; (b) an aqueous solution of sulfuric acid, nitric acid, phosphoric acid or acetic acid; or (c) glacial acetic acid, to yield a modified cellulose. This modified cellulose, referred to as "microfibrillated oxycellulose," can be isolated as a fine powder. As used herein, the term "microfibrillated oxycellulose" is intended to refer to a white or off-white oxycellulose product which can be readily isolated as, or converted into, a fine powder or friable aggregates, or into an aqueous dispersion, which can be colloidal. The term "microfibrillated oxycellulose" is thus also intended to exclude products from processes which yield long resilient unruptured fibers which are not friable or water dispersible.

Therefore, the present invention provides a method whereby persulfate can be readily and economically used to convert cellulosic materials, such as purified cotton, paper, cotton linters, α-cellulose, wood pulp, purified wood pulp, or like materials, into microfibrillated oxycellulose. The microfibrillated oxycellulose can serve as a carrier or cocarrier for a wide variety of acidic, neutral or basic bioactive compounds or cosmetic compounds in novel film-forming systems for application to skin or hair, thereby producing substantive, controlled and/or sustained topical and transdermal formulations which have superior cosmetic and elegance features. Such formulations may be devoid of fats, waxes, oils or surfactants, thereby producing hypoallergenic and non-irritating topical systems. The present method also affords an oxycellulose that is compatible with chemicals containing free amine group(s). The present microfibrillated oxycellulose is biocompatible and resistant to color reversion during storage at room temperature. At elevated temperatures (higher than 45° C.), the tendency of the material to darken slightly varies, and depends on the reaction conditions used for its preparation. The present microfibrillated oxycellulose can be used in the preparation of sustained solid oral dosage forms (e.g., as a binder and disintegrant in the making of tablets). The microfibrillated oxycellulose can be used to form completely aqueous or substantially aqueous (water miscible solvents may be incorporated) colloidal or near-colloidal suspensions which are capable of incorporating high concentrations of crystalline and non-crystalline water-soluble or insoluble materials. These suspensions can produce monolithic films. Conventional formulation procedures can be used to prepare cream, gel, lotion, and spray products utilizing the present microfibrillated oxycellulose.

Preferably, a minimum of 10 ml or a maximum of 12.5 ml of aqueous acetic acid or other acid is needed per gram of cellulose (as cotton linter). The weight-to-weight ratio of cellulose material to the persulfate salt can range from about 1:0.1 to about 1:3, 1:0.5 to 1:1.0 being the presently preferred ratio when reaction carried out in glacial or aqueous acetic acid. For other acids, such as inorganic mineral acids, the ratio of cellulose material to persulfate salt ranges from 1:2 to 1:6, although the presently preferred ratio is 1:2 to 1:3. The apparent concentration of the persulfate in the water-mediated reaction ranges between about 0.85 and 2.5M, depending on the amount of persulfate added.

The degree of oxidation and the type of functional groups that are introduced by the persulfate depend on the reaction conditions used. In acid solutions, the formation of sulfur tetraoxide as an intermediate has been proposed. In dilute acid conditions, sulfur tetraoxide dissociates to give sulfur trioxide and nascent oxygen, whereas in a concentrated acid medium, Caro's acid ($H_2SO_5$) is formed. Thus, by way of explanation and without limitation, the formation of oxycellulose using persulfate may occur as a result of the attack by sulfur tetraoxide, sulfate anion radicals, and/or nascent oxygen on the anhydroglucose unit of the cellulose molecules, and by concurrent acid-catalyzed hydrolytic cleavage of the β-1,4 glycosidic linkages. Further, the presence of acid in the reaction mixture may lead to oxycellulose that may contain hydrocellulose molecules as well as oxycellulose molecules of varying degrees of polymerization. However, as used herein, the term "microfibrillated oxycellulose" encompasses all of these embodiments of the modified cellulose of the invention. Percentages are by weight unless otherwise indicated.

BRIEF DESCRIPTION OF THE DRAWINGS

Further features and advantages of the invention will become apparent upon studying the following description in conjunction with the following drawings in which.

DETAILED DESCRIPTION OF THE PREFERRED EMBODIMENTS

Figure 1:
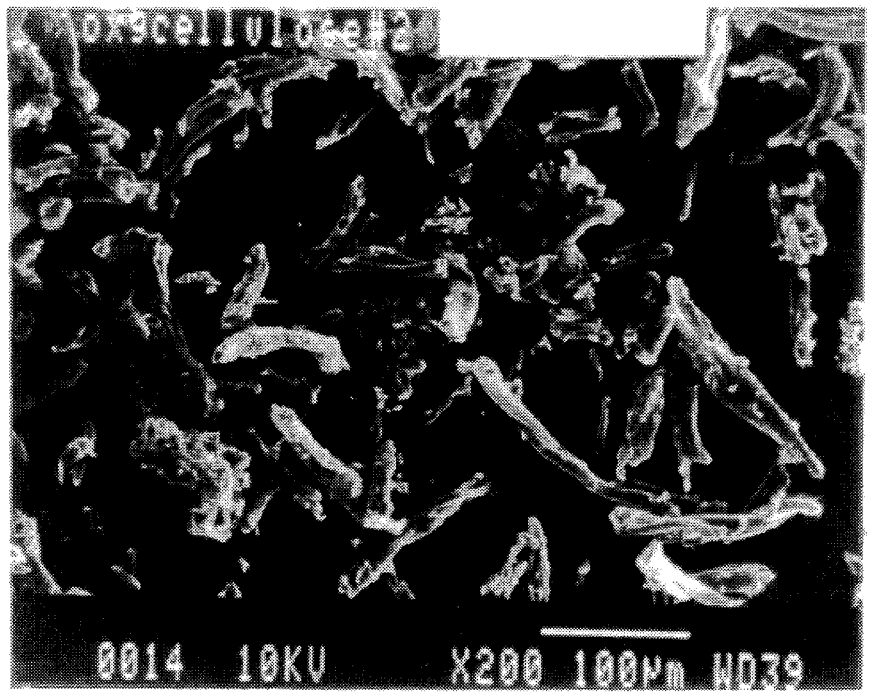
FIGS. 1 and 2 are scanning electron micrographs (SEM) of the oxycellulose products prepared using 1:3 and 1:5.4 ratio of cotton linters to sodium persulfate in water and a cotton linters-to-water ratio of 1:10 (w/v).

More specifically, the present method comprises heating a reaction mixture of a suspended cellulosic material and a persulfate salt, such as ammonium, sodium, or potassium persulfate to obtain microfibrillated oxycellulose. The concentration of the persulfate salt in the water-mediated reaction mixture is about 0.85–2.5M, based on the amount of persulfate added. An aqueous persulfate solution of concentration as low as about 0.6–0.7M (i.e., 0.63M) with a weight-to-volume ratio of cellulose material to water of about 1:20–30, can also be used. The reaction mixture is then heated to about 70°–125° C., preferably with agitation, for a period of time effective to oxidize the cellulosic material to the desired microfibrillated oxycellulose, e.g., about 2–48 hours, preferably about 3–18 hours. At temperatures of about 25°–65° C., for example, reactions can take from several days to months for completion, and can yield undesirably fibrous products. Therefore, such lower temperatures are not preferred for the practice of the present method.

Preferably, the water-mediated reaction is carried out in the presence of an aqueous inorganic acid such as sulfuric, nitric, or phosphoric acid or an organic acid such as aqueous or glacial acetic acid. Hydrochloric acid can be used, but is less preferred. Preferably, the water-mediated reaction is carried out at a pH of less than 4.0, preferably less than 3.0 to 3.5, with a pH range from 0.1 to 2.0 most preferred. The use of acid in the reaction mixture improves whiteness (e.g., from off-white product to white), alkali-staining resistance, and the compatibility of the microfibrillated oxycellulose with compounds that contain free amine group(s). The improvement of these properties tends to increase with an increase in the concentration of the acid being used.

The preferred snow-white microfibrillated oxycellulose can be prepared utilizing sulfuric acid, nitric acid, phosphoric acid, or acetic acid solutions at concentrations of as low as about 1.25N, about 1.25N, about 10N, or about 40% (v/v)(about 6.7M), respectively, whereas to produce an alkali-staining resistant oxycellulose product, a solution having a minimum concentration of about 1.50N sulfuric acid or nitric acid and about 10N phosphoric acid, is required. Reaction mixtures containing phosphoric acid at a concentration of equal to or higher than about 12N yield oxycellulose products which, when neutralized, show the greatest compatibility with drugs or chemicals that contain free amine group(s).

Microfibrillated oxycellulose prepared using glacial acetic acid is colorless and resistant to staining by alkali. An oxycellulose product, prepared using a weight ratio of about 1:0.1–0.2 of cellulose to persulfate salt and a weight-by-volume ratio of about 1:10 of cellulose to glacial acetic acid, is unexpectedly compatible with amine-containing chemicals/drugs such as benzocaine, phenylpropanolamine and the like.

The compatibility of the product with drugs that contain free amine group(s) is monitored by mixing a small quantity of the material with benzocaine or phenylpropanolamine in water, and allowing the mixture to stand at room temperature (25° C.) for several days. If the mixture develops any color during storage, the test material is then regarded as incompatible with the oxycellulose. The formation of colored imine complex(es) is assumed to be due to the interaction between an aldehyde and/or a ketone group of the oxycellulose and an amine group of the drug.

Although the persulfate salt necessarily contains a metal counter ion, the present method is preferably accomplished without the presence of non-persulfate metal salts. Such salts have been used in other oxidative methods to catalyze the decomposition of persulfate. Such excluded metal salts include, but are not limited to, the halide, nitrate, phosphate, acetate, oxalate, or sulfate salts of transition metals such as copper, iron, cobalt, silver, nickel, manganese, chromium, titanium and the like.

Isolation of the microfibrillated oxycellulose from the reaction mixture can be readily accomplished by filtration, preferably followed by washing the residue with water, then with a water-miscible solvent such as a lower alkanol, followed by washing with a volatile solvent, such as acetone, methyl ethyl ketone or the like. If reaction conditions that yield alkali-stain resistant microfibrillated oxycellulose are used, the residue is then preferably washed with water and the dilute aqueous solution of a base such as sodium or potassium hydroxide to neutrality, followed by a water wash and the solvent washes.

Figure 2:
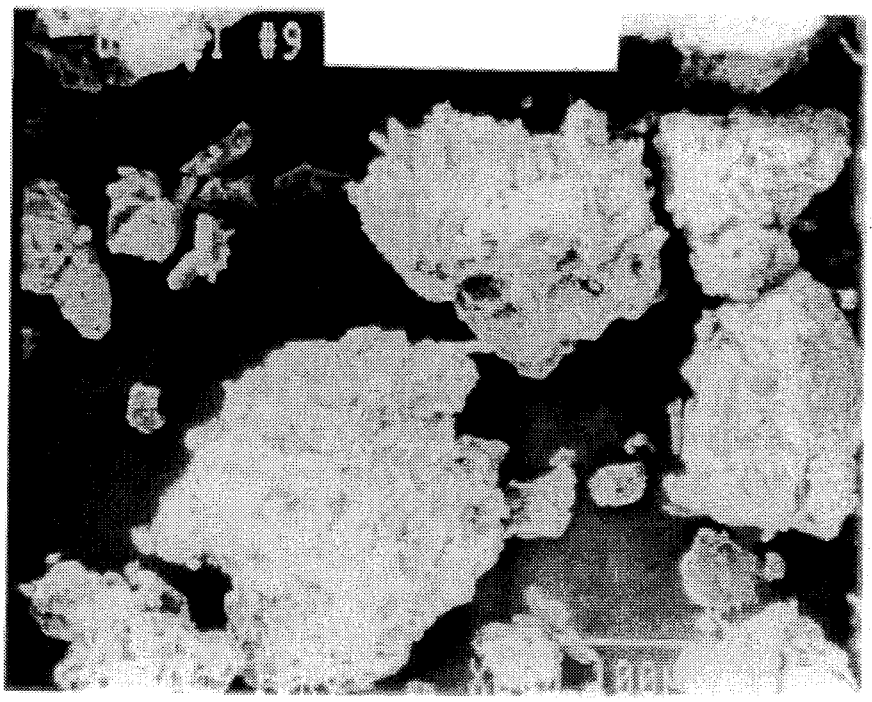
Figure 3:
FIGS. 3–6 are photomicrographs (170x or 200x) that show the size of the fiber fragments of an oxycellulose product prepared using a 1:3 ratio of cotton linters-to-sodium persulfate in about 1.25N sulfuric acid, about 12.0N phosphoric acid, glacial acetic acid and about 50% (v/v) aqueous acetic acid, respectively.
Figure 4:
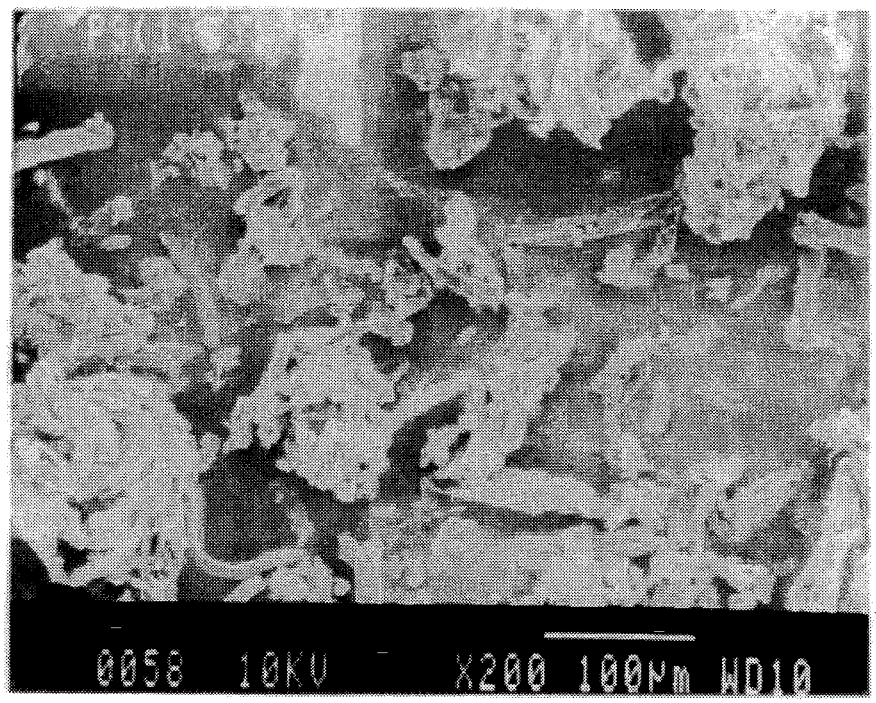
Figure 5:
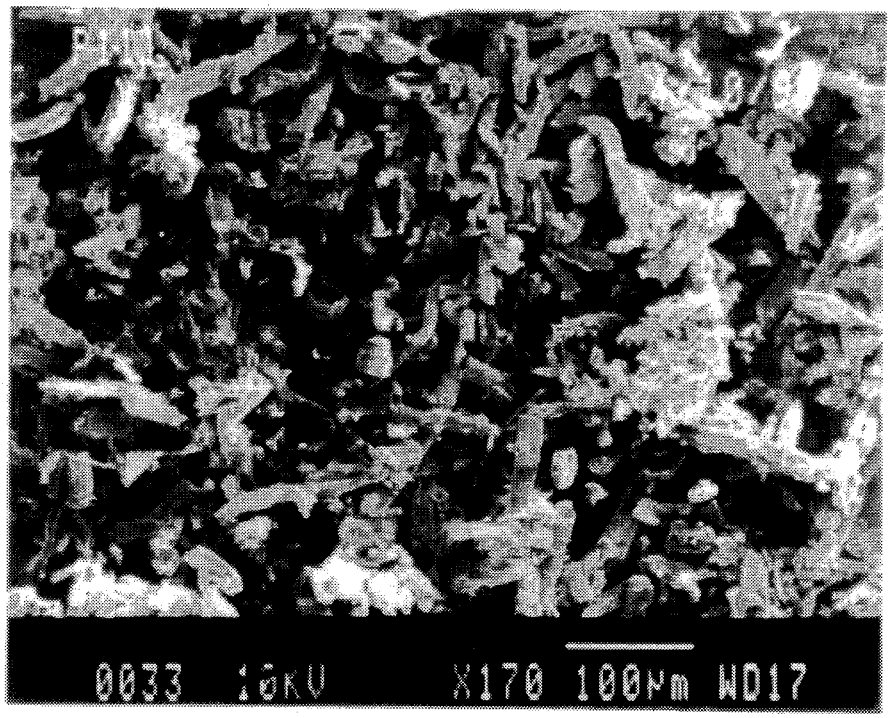
Figure 6:

Scanning electron micrographs (SEM) of the oxycellulose products prepared using 1:3 and 1:5.4 ratio of cotton linters to sodium persulfate in water and a cotton linters-to-water ratio of 1:10 (w/v), are shown in FIGS. 1 and 2, respectively. As is evident from FIG. 2, a significant reduction in the fiber fragment size occurs in the presence of the larger amount of persulfate.

FIGS. 3–6 are photomicrographs (170x or 200x) that show the size of the fiber fragments of an oxycellulose product prepared using a 1:3 ratio of cotton linters-to-sodium persulfate in about 1.25N sulfuric acid, about 12.0N phosphoric acid, glacial acetic acid and about 50% (v/v) aqueous acetic acid, respectively. Satisfactory products were obtained using each of these sets of reaction conditions.

The typical preparative method involves heating of a suspension of the cellulosic material, such as the cotton linters (sheet or pulp) and the persulfate salt in glacial acetic acid, water or an aqueous solution of acetic acid, phosphoric acid, nitric acid or sulfuric acid, preferably at about 70°–125° C., for a period of time sufficient to convert the cellulosic material into microfibrillated oxycellulose. The reaction time is dependent on the factors discussed above, and can be determined by sequentially working up small portions of the reaction mixture. After, for example, about 3–18 hours, filtration, followed by washing the finely divided residue, first with water, and if a dried powder is sought, with an organic solvent such as methanol and/or acetone, affords the desired oxycellulose product.

Microfibrillated oxycellulose prepared using reaction mixtures containing glacial acetic acid, at least about 1.5N aqueous sulfuric or nitric acid, or about 10N phosphoric acid are resistant to staining by alkali. Therefore, if desired, the white residue left after filtration can be washed with an aqueous base such as aqueous potassium hydroxide to near neutral pH, followed by washes with water and a volatile organic solvent such as acetone.

The oxycellulose products, in their final stages of the washing with water, begin to convert to a colloidal to semi-colloidal state, which causes the filtration to become very slow and difficult. This problem, however, can be eliminated by washing the residue with small volumes of water. An aqueous dispersion of the neutralized and washed oxycellulose solids, obtained in this manner, shows a pH value near neutral (6.5–7.5), whereas the pH of an aqueous suspension of oxycellulose material that was not washed with potassium hydroxide is about 4–6.

The yield of the oxycellulose product decreases with an increase in the concentration of persulfate in the reaction, and is unaffected by the concentration of sulfuric acid, within the useful range. In the case of nitric acid, the yield remains about the same at lower concentrations of acid, but increases at concentrations above about 1.0N. The similar trend to that observed with nitric acid is noted with phosphoric acid. Yields of oxycelluloses range from 65–75% in the concentration range of $\leq 4.0N$ acid and are about 85% at concentrations $\geq 4.0N$ acid. In glacial acetic acid, the yield of the oxycellulose product is about 85–95%, and in aqueous acetic acid solutions (about 5–85% by volume acetic acid), the yield is about 70–90%.

The number of carboxylic groups introduced in the product increases with increasing persulfate concentration. The oxycellulose product prepared in water using a 1:3 ratio of cotton linters-to-sodium persulfate and a 1:10 wt/vol. ratio of cotton linters to liquid phase contains about 1.05–1.71% of the carboxylic acid functionality, and about 4.2–5.6% of carbonyl groups. The presence of about 0.05–1.75N sulfuric acid, about 0.05–1.0N nitric acid or about 1.0–15N phosphoric acid appears to have no appreciable affect on the carboxylic content of the product. A decrease in the amount of carboxylic groups, however, is noted at higher acid concentrations (i.e., above about 2N $H_2SO_4$, 1.25N $HNO_3$ or about 15N phosphoric acid. The amount of the carbonyl groups (i.e., aldehyde and/or ketone groups) in the product tends to decrease with an increase in the concentration of the acid as indicated by the less and less intense color formation upon treatment of the product with phenylpropanolamine or benzocaine. Materials from aqueous acetic acid contain some aldehyde and/or ketone groups as indicated by the color test, whereas products from glacial acetic acid show only traces of these functionalities. An oxycellulose product prepared from a reaction containing about 1:0.1–0.2 weight ratio of cotton linters-to-persulfate in glacial acetic acid is essentially free of reactive functional groups.

Conventional formulation procedures can be used to prepare cream, lotion and spray products utilizing the present microfibrillated oxycellulose. For example, ingredients can often be simply mixed using a mechanical stirrer, followed by homogenization of the mixture. Also, heated oil and the aqueous phases can be prepared separately, combined and the resultant blend allowed to cool to room temperature with constant agitation.

An aqueous dispersion of the oxycellulose can be readily prepared by stirring the dry powdered material or the wet product (before washing with acetone or methanol), in an appropriate amount of water. A conventional laboratory mechanical stirrer, a homogenizer or a household blender is satisfactory to make a homogenous dispersion of the oxycellulose. However, dispersions with substantially higher percentages of oxycellulose can be made using a high-shear mixer/homogenizer or like equipment.

Aqueous dispersions containing above about 20%, e.g., between about 20–30% oxycellulose, by weight, are creams, whereas dispersions containing about 7.5–20% of oxycellulose are generally either viscous liquids or thixotropic gels. If desired, a stable dispersion containing oxycellulose content ranging from 7.5% to as low as 1.0% or less can be made using 0.25%–2.5% of a water-insoluble suspending agent such as microcrystalline cellulose, bentonite, smectite clays, fumed silicas, or modified clays (Thixogel). Any appropriate water-soluble, organic thickening agent, such as methyl cellulose, hydroxypropyl cellulose, hydroxypropyl methyl cellulose, carboxymethylcellulose, PVP, polyacrylates, alginates, or the like can also be used in the same amount. Useful agents of these classes are disclosed in U.S. Pat. No. 4,569,861, the disclosure of which is incorporated by reference herein. A minor but effective amount of a surfactant such as a polysorbate and/or a poloxamer can also be used to assist formation of the dispersions. The viscosity of the dispersion increases with a decrease in the size of the particles being suspended.

Preferably, the oxycellulose is resuspended in water, optionally with a water-miscible organic solvent, together with an effective amount of one or more active ingredients to form a dispersion, gel or cream. Active ingredients may be selected from a wide variety of cosmetics, pharmaceuticals, insecticides, herbicides, rodenticides, fungicides, pigments, insect repellants or fragrance.

Oxycellulose dispersions comprising such active ingredients can be physically, chemically, and microbiologically stable at room temperature for many months. It is, however, preferred to add minor but effective amounts of one of the commonly used biocidal preservatives such as the phenols, benzoates, parabens, quats (quaternium-15) and the like, to increase resistance and/or inhibition of any microbial growth.

Irrespective of the amount of oxycellulose present, these dispersions produce extremely adhesive films on the human skin. If desired, minor but effective amounts of glycerin, propylene glycol, mineral oil, citric acid, esters, N,N-m-diethyltoluamide, and the like can be used to plasticize the films. When plasticized, all dispersions form transparent, non-tacky, and non-oily films. The plasticized dispersion, optionally with other conventional ingredients, can also be cast to form a dimensionally stable drug containing film or "patch" that offers potential use in the development of prolonged release transdermal therapeutic systems.

The solid oxycellulose can also be compressed, preferably without the presence of a binder, to form a pill or tablet, wherein the oxycellulose acts both as a highly effective binder and a disintegrant. Other potential applications of the product include the preparation of long lasting perfume and fragrance formulations, and sustained release insecticides, insect repellants, rodenticides, fungicides, and herbicides. Dispersions of the microfibrillated oxycellulose may be freeze dried, spray dried, and cast as films or matrices, to produce products with a wide range of structural properties for many other cosmetic, agricultural, and pharmaceutical applications.

The preparations of oxycellulose and its applications in the formulations of a variety of topical and transdermal drug products are illustrated by the following examples, which are not to be construed as limiting.

EXAMPLE 1

Acid-Free Oxidation of Cellulose with Persulfate

A. Six hundred grams (2.52 moles) of sodium persulfate and 200 grams of cotton linter sheet, broken into small pieces, were placed in a two-gallon container and two liters of water were added (1.26M persulfate concentration). The container was then placed in a water bath that had been adjusted to 70°–75° C. The reaction mixture was initially stirred with a glass rod, and once the cotton linter pieces were broken into a finely divided powder, the stirring was performed using a mechanical stirrer equipped with a polyethylene shaft and blade. The reaction was considered complete when the gas evolution from the reaction mixture completely ceased (about 3–4 hours). The reaction mixture was filtered, and the white residue was first washed with water, then with methanol, and finally, with acetone to provide the microfibrillated oxycellulose product in 70–75% yield.

B. A similar reaction run using 400 g of sodium persulfate (0.84M) also yielded a satisfactory oxycellulose product.

EXAMPLE 2

Oxidation of Cellulose in Dilute Aqueous Acid

Sodium persulfate and cotton linters in two liters of 50:50 (v/v) acetic acid:water mixture, 1.26N sulfuric acid or nitric acid solution, or of 15.0N phosphoric acid solution, were reacted according to the procedure of Example 1A or 1B. In the case of sulfuric acid-, acetic acid- and nitric acid-treated reaction mixtures, the white microfibrillated oxycellulose product which formed was filtered, and then washed sequentially with water and acetone. The phosphoric acid-treated reaction mixture was first diluted with water, and then filtered. The white residue, left after filtration, was washed with an additional 100–150 ml of water. The wet solid was then resuspended in water, and neutralized with 2.0N aqueous potassium hydroxide. The suspension was then filtered, and the oxycellulose residue was washed with water to remove inorganic salts. A final wash of the residue with acetone (150–200 ml), followed by drying in air, provided white microfibrillated oxycellulose in 70–85% yield.

EXAMPLE 3

Oxidation of Cellulose in Glacial Acetic Acid

Ten grams of cotton linters, broken into small pieces, and 2.0 g sodium persulfate were placed in a 250 ml two-neck round bottom flask that had been equipped with a reflux condenser and a stopper. About 100 ml (1.67 moles) of glacial acetic acid was added, and the mixture was then heated at 120°–125° C., with occasional shaking, until the cotton linter pieces were broken into finely divided fibers. The stopper was then replaced with a mechanical stirrer, and the heating was continued, with stirring, for about 2.5 hours. The reaction mixture was filtered, and the white solid was washed first with water, then with methanol, and finally with acetone. The white solid was air dried and ground to provide microfibrillated oxycellulose in 92–95% yield.

EXAMPLE 4

Aqueous Dispersions of Oxycellulose

Sodium persulfate and the cotton linters were treated in the same manner as described in Examples 1, 2, or 3. The dry oxycellulose powder or the wet residue, left after washing with water to a neutral pH, was transferred into a beaker. To this residue was added methyl paraben and propylparaben, equivalent to 0.15% and 0.10% of the oxycellulose, respectively. An appropriate amount of water was added, and a homogenous colloidal dispersion of the oxycellulose was obtained by stirring for about 30–45 minutes, using either a conventional stirrer or a higher shear mixer. For example, dispersions were prepared comprising 20% or 26.2% oxycellulose. The oxycellulose dispersions prepared using the product that was not washed with potassium hydroxide, exhibited pH of about 4–6. If desired, the oxycellulose dispersion prepared in this manner can be neutralized with an aqueous solution of sodium hydroxide or potassium hydroxide or with an alkanolamine such as triethanolamine.

EXAMPLE 5

Insect-Repellant Lotion

The procedures of Examples, 1, 2 or 3, and 4, were repeated to form 20% aqueous oxycellulose dispersions. To a stirred mixture of 25 grams of the dispersion of 56 ml of water was added 0.5 grams of a cross-linked polyacrylic acid (Carhomer 934P, Goodrich). After the Carhomer 934P was completely dissolved, 0.11 grams of methyl paraben, 0.08 grams of propyl paraben, and 2.50 grams of glycerin were added. The mixture was then neutralized with triethanolamine (0.50 grams). An immediate increase in the viscosity occurred. To the mixture was then added 15.00 grams of N,N-diethyl-m-toluamide, and the resultant mixture was stirred for an hour. The resulting lotion is stable at room temperature and at 42° C. It forms a transparent, non-tacky, and non-oily film upon application to the human skin, and provides an effective protection from insects.

EXAMPLE 6

Skin Cream

A cosmetically elegant cream product, which is as effective as the insect repellant lotion product, was prepared following the procedure of Example 5, except that 0.50% of hydroxypropyl cellulose was added after dissolving Carbomer 934P in the formulation. A number of other commonly used thickening agents, such as hydroxypropyl methyl cellulose, methyl cellulose, hydroxypropyl ethyl cellulose, and the like, can be used as well.

EXAMPLE 7

Insect Repellant Spray

The procedures of Examples 1, 2 or 3, and 4 were repeated to form a 20% oxycellulose dispersion. Carbomer 934P (0.25 grams) was dissolved in a suspension of oxycellulose dispersion (25 grams) in 40 ml of water-ethanol mixture (1:1, w/w). To the mixture were then sequentially added methyl paraben (0.11 grams), propyl paraben (0.08 grams), triethanolamine (0.25 grams), and N,N-m-diethyltoluamide (15.00 grams). The suspension was then stirred for an hour. The resulting product can be packaged as an aerosol or pump spray product. When sprayed on the human skin, it dries in about 2–3 minutes, forming an invisible, non-tacky, and non-oily film.

EXAMPLE 8

Drug-Delivery Patch

The procedures of Examples 1, 2 or 3, and 4 were repeated to form an oxycellulose dispersion that contained 26.2% oxycellulose, 0.15% methyl paraben, and 0.10% propyl paraben. The resultant oxycellulose dispersion (60.8 g) was placed in a beaker, and diluted with 15.8 grams of water. To a thoroughly mixed dispersion was then added 1.0 gram of hydroxypropyl cellulose. When the hydroxypropyl cellulose was completely dissolved, 0.22 grams of methyl paraben, 0.14 grams of propyl paraben, 6.0 grams of glycerin, and 16.0 grams of nitroglycerin-polyethylene glycol (9:1) were added. The suspension was stirred for an additional one or two hours. The resulting formulation was cast to form a tack-free and flexible drug-delivery film or "patch."

The invention has been described with reference to various specific and preferred embodiments and techniques. However, it should be understood that many variations and modifications may be made while remaining within the spirit and scope of the invention.

What is claimed is:

1. A dispersion comprising about 7.5% to 20% by weight of microfibrillated oxycellulose made in accordance with a method which comprises:

heating a reaction mixture comprising a suspension of a cellulose material and a persulfate salt in an acid, the mixture having a weight-ratio of cellulosic material to persulfate salt of about 1:0.1–3, at a temperature of about 70°–125° C., for a period of time effective to convert the cellulose material into microfibrillated oxycellulose; and isolating the microfibrillated oxycellulose from the reaction mixture.

2. A dispersion in accordance with claim 1 additionally comprising a minor but effective amount of a plasticizer.

3. A cream comprising a dispersion of at least about 20% by weight of a microfibrillated oxycellulose made in accordance with a method comprising:

heating a reaction mixture comprising a suspension of a cellulose material and a persulfate salt in an acid, the mixture having a weight-ratio of cellulosic material to persulfate salt of about 1:0.1–3, at a temperature of about 70°–125° C., for a period of time effective to convert the cellulose material into microfibrillated oxycellulose; and isolating the microfibrillated oxycellulose.

4. A method in accordance with claim 1 wherein the reaction mixture additionally comprises glacial acetic, or aqueous sulfuric, phosphoric, hydrochloric or acetic acid.

5. The method of claim 4 wherein the acid is acetic acid and the weight-volume ratio of cellulosic material to acetic acid ranges from about 1:10 to about 1:12.5.

6. The method of claim 4 further comprising washing the microfibrillated oxycellulose with water and aqueous base.

7. The method of claim 6 wherein the aqueous base is an aqueous alkali metal hydroxide.

8. A dispersion in accordance with claim 1 wherein the dispersion is a thixotropic gel.

9. A method of making a dispersion comprising:

heating a reaction mixture comprising a suspension of a cellulose material and a persulfate salt in an acid, the mixture having a weight-ratio of cellulosic material to persulfate salt of about 1:0.1–3, at a temperature of about 70°–125° C., for a period of time effective to convert the cellulose material into microfibrillated oxycellulose;

isolating the microfibrillated oxycellulose from the reaction mixture; and dispersing about 0.25–2.5% of a water-insoluble suspending agent and about 1–7.5% of microfibrillated oxycellulose in a liquid medium.

10. A method in accordance with claim 9 wherein the reaction mixture additionally comprises glacial acetic, or aqueous sulfuric, phosphoric, hydrochloric or acetic acid.

11. The method of claim 10 wherein the acid is acetic acid and the weight-volume ratio of cellulosic material to acetic acid ranges from about 1:10 to about 1:12.5.

12. The method of claim 11 further comprising washing the microfibrillated oxycellulose with water and aqueous base.

13. The method of claim 12 wherein the aqueous base is an aqueous alkali metal hydroxide.

14. A method for making a dispersion having about 0.25–2.5% of a water-soluble thickening agent and about 1–7.5% of the microfibrillated oxycellulose made in accordance with a method of making microfibrillated oxycellulose comprising:

heating a reaction mixture comprising a suspension of a cellulose material and a persulfate salt in an acid, the mixture having a weight-ratio of cellulosic material to persulfate salt of about 1:0.1–3, at a temperature of about 70°–125° C., for a period of time effective to convert the cellulose material into microfibrillated oxycellulose;

isolating the microfibrillated oxycellulose from the reaction mixture; and dispersing sufficient amounts of a microfibrillated oxycellulose and a water soluble thickening agent in a liquid medium to obtain a dispersant containing about 0.25–2.5% of a water soluble thickening agent and about 1–7.5% microfibrillated oxycellulose.

15. A method in accordance with claim 14 wherein the acid is glacial acetic, or aqueous sulfuric, phosphoric, hydrochloric or acetic acid.

16. A dispersion comprising an effective amount of a cosmetic, a pharmaceutical, an insecticide, a rodenticide, an insect repellant, a fungicide, a fragrance or a pigment as an active ingredient in a dispersion made in accordance with claim 15.

17. A dispersion in accordance with claim 1 wherein the dispersion comprises an effective amount of a cosmetic, a pharmaceutical, an insecticide, a rodenticide, an insect repellant, a fungicide, a fragrance or a pigment as an active ingredient.

* * * * *